US00PP10632P

United States Patent [19]

Pouw

[11] Patent Number: Plant 10,632

[45] Date of Patent: Oct. 6, 1998

[54] HYBRID TEA ROSE PLANT NAMED 'RUIAB'

[75] Inventor: A.A. Pouw, De Kwakel, Netherlands

[73] Assignee: DeRuiter's Nieuwe Rozen B.V., Netherlands

[21] Appl. No.: 789,833

[22] Filed: Jan. 28, 1997

[51] Int. Cl.[6] ..... A01H 5/00

[52] U.S. Cl. ..... Plt./16

[58] Field of Search ..... Plt./11, 16, 17

[56] References Cited

U.S. PATENT DOCUMENTS

P.P. 2,999 11/1970 Kordes ..... Plt./16

*Primary Examiner*—Howard J. Locker

*Attorney, Agent, or Firm*—Christie, Parker & Hale, LLP

[57] ABSTRACT

A new variety of Hybrid Tea rose plant producing apricot-ochre flowers of good form and suitable for growing under glass.

2 Drawing Sheets

BACKGROUND OF THE INVENTION

The present invention relates to a new and distinct variety of rose plant of the hybrid tea rose class which was created by crossing undistributed, unnamed and unpatented seedlings as seed and pollen parents in De Kwakel, Holland. The varietal denomination of the new variety is 'Ruiab'. The new variety was isolated and asexually reproduced by budding in Holland.

SUMMARY OF THE INVENTION

Among the novel characteristics possessed by this new variety which distinguish it from its parents and all other varieties of which I am aware are its attractive apricot-ochre flowers of good form borne on a floriferous plant with long stems and suitable for production of cut flowers under glass. The new variety has been reproduced through propagation by cuttings, grafting, budding and micropropagation.

Asexual reproduction by budding of the new variety as performed in De Kwakel, Holland, shows that the foregoing and other distinguishing characteristics come true to form and are established and transmitted through succeeding propagations.

BRIEF DESCRIPTION OF THE ILLUSTRATIONS

The accompanying photographic illustrations show typical specimens of the vegetative growth and flowers of the new variety in different states of development depicted in color as nearly true as it is reasonably possible to make the same in color illustrations of this character.

Sheet 1 is a close up view of the bloom.

Sheet 2 illustrates foliage, stems, and flowers of the new cultivar at various stages of maturity.

DESCRIPTION OF THE NEW VARIETY

The following is a detailed description of the new variety, with color terminology in accordance with The Royal Horticultural Society Colour Chart (RHSCC) and horticultural terminology in accordance with standard terminology used in UPOV-approved horticultural guideline. The terminology used in color descriptions herein refers to plate numbers in the aforementioned color chart. Phenotypic expression may vary depending upon growing conditions under different climate, soil, and cultivation conditions.

Parentage: Seed and pollen parents are seedlings.

Class: Hybrid Tea.

As can be seen in Sheet 2 there is shown a new shoot, 1; compound three, five and seven leaflet leaves, 2, 3 and 4, respectively; a stem, 5; buds, 6 and 7; a flower, 8, about one-third open; and a flower, 9, more fully open. Also shown are flower stems 10, 11 and 12, with reproductive organs displayed.

The following further horiticultural description is based on observations made of specimens grown under glass in De Kwakel, Holland.

Flower

Blooming habit: Nearly continuous.

A. Bud:

(1) *Size*.—Medium, about 3 to 4 cm long and about 2 to 3 cm wide.

(2) *Form*.—Ovate (shape of longitudinal section just before separation of sepals); urn-shaped after sepals part.

(3) *Color*.—As sepals divide, near 15C to 15D with occasional red streak or blush.

(4) *Sepals*.—About same length as bud; upper side near 148C and near 176A at the points; underside near 146C and near 174A at the points; spread then reflex back.

(5) *Peduncle*.—Long: Strength-erect, strong. Color-medium green, near 146B to 146C with brownish tinge.

B. Bloom:

*Flower*.—Medium; viewed from above — star-shaped; viewed from side — (a) upper part of fully opened flower, flattened convex; (b) lower part of fully opened flower, concave.

(1) *Size*.—Average size when fully expanded — about 8 to 10 cm.

(2) *Borne*.—Singly, one to a stem.

(3) *Form*.—Pointed center, exhibition type, spiral imbricated, outer petals reflex to points.

(4) *Petalage*.—Fully double, about 22.

(5) *Color*.—After sepals part and petals unfurl color of petal top surface appears near 23C; (⅓ to full open) inner petals near 23B lighter at edge, outer petals lighter coloration. Undersurface is near 19A with near 17D at base. Undersurface of aged flowers is near 27B to 27C and near 17D at base. Overall tonality from a distance is attractive apricot-ochre;

upper surface of aged flower near 36B with near 17D at base.

(6) *Peduncle*.—Generally smooth.

(7) *Fragrance*.—Weak.

(8) *Length of stems**.—About 60 cm.

(9) *Production**.—About 220 flowers per $m^2$ per year.

*Averages only, depends on circumstances of cultivation.

C. Petals:

(1) *Texture*.—Crisp.

(2) *Appearance*.—Inside velvety and outside satiny.

(3) *Form and size*.—Broad, medium, and the petal margin reflects to points.

(4) *Arrangement*.—Regularly arranged, imbricated.

(5) *Petaloids*.—About nine, of which approximately five are about 3.5×4 cm and approximately four very small approximately 2×1.5 cm.

(6) *Lasting quality*.—Long-lasting quality on plant and after cutting; about 15 days after cutting, about 20 days on plants.

Reproductive Organs

A. Stamens, filaments and anthers:

*Arrangement and color*.—Regularly arranged around styles; color of filaments — yellow.

B. Pollen:

*Color*.—Orange, near 25A.

C. Styles: Long, stigma above mouth of receptacle, yellow.

D. Stigmas: Orange, positioned below anthers.

E. Hip: Funnel-shaped; medium seed vessel at petal fall.

Plant

A. Form: Narrow, bushy, average disease resistance; plant height about 1.7 meters, plant width about 0.6 meters.

B. Growth: Vigorous.

C. Foliage: Compound 3, 5 and 7 leaflets.

(1) *Size*.—Medium width and length.

(2) *Quantity*.—Abundant.

(3) *Color*.—Juvenile foliage — red purple to bronze-reddish; near 181A to 181B; undersurface near 181A; weak anthocyanin coloration, (shoot about 20 cm long); mature leaf color — near 136A top surface; near 147B undersurface.

(4) *Shape*.—Broad oval.

(5) *Texture*.—Upper side is medium glossy underside is matte.

(6) *Edge*.—Serrate.

(7) *Serration*.—Ordinary, acuminate apices.

(8) *Leaf stem*.—Color — near 147A to 147B.

(9) *Stipules*.—Short, simple, medium green, distinct auricle.

(10) *Leaflets*.—Cross section — slight concave: weak undulation of margin; terminal leaflet — short length and medium length; blade and about 7 to 8 cm long and 5 to 6 cm wide, rounded base.

D. Wood:

(1) *New wood*.—Color — young shoots have weak to medium anthocyanin; coloration — bronze red purple to reddish brown.

(2) *Old wood*.—Color — near 147A to 147B.

E. Prickles (thorns):

(1) *Prickles*.—Present; quantity (main stalk) — ordinary; shape of lower side — concave; Length — short prickles absent or very few, long prickles few to medium; Color — near 159A; Position — irregular.

What is claimed is:

1. A new and distinct variety of rose plant of the Hybrid Tea rose class, substantially as shown and described.

* * * * *

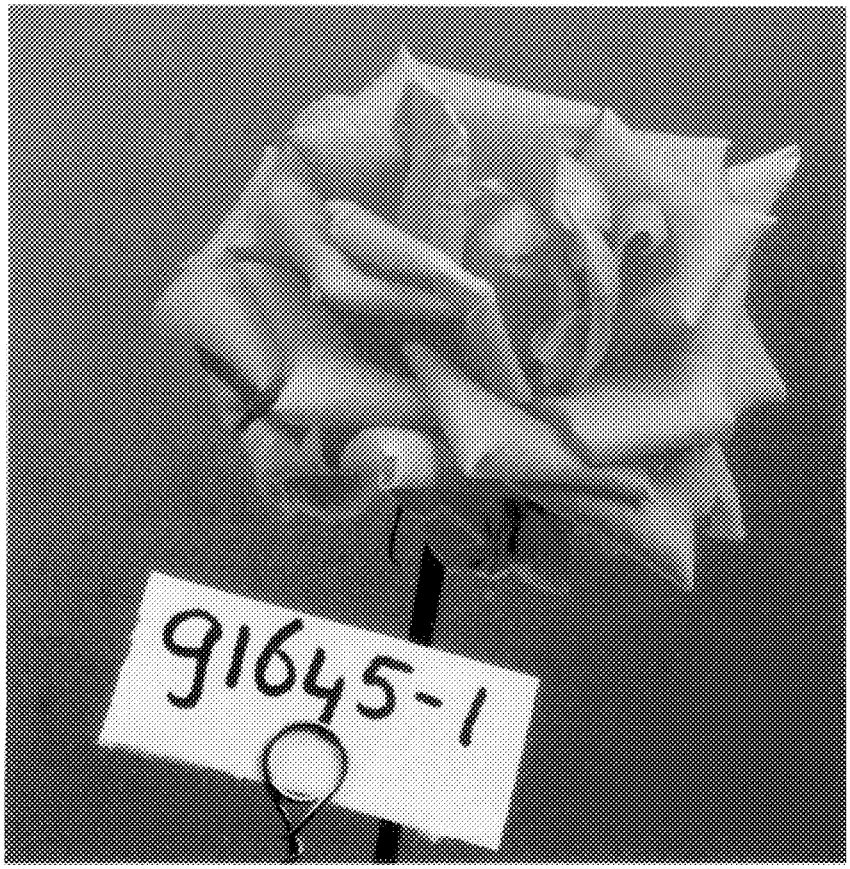
91645-1

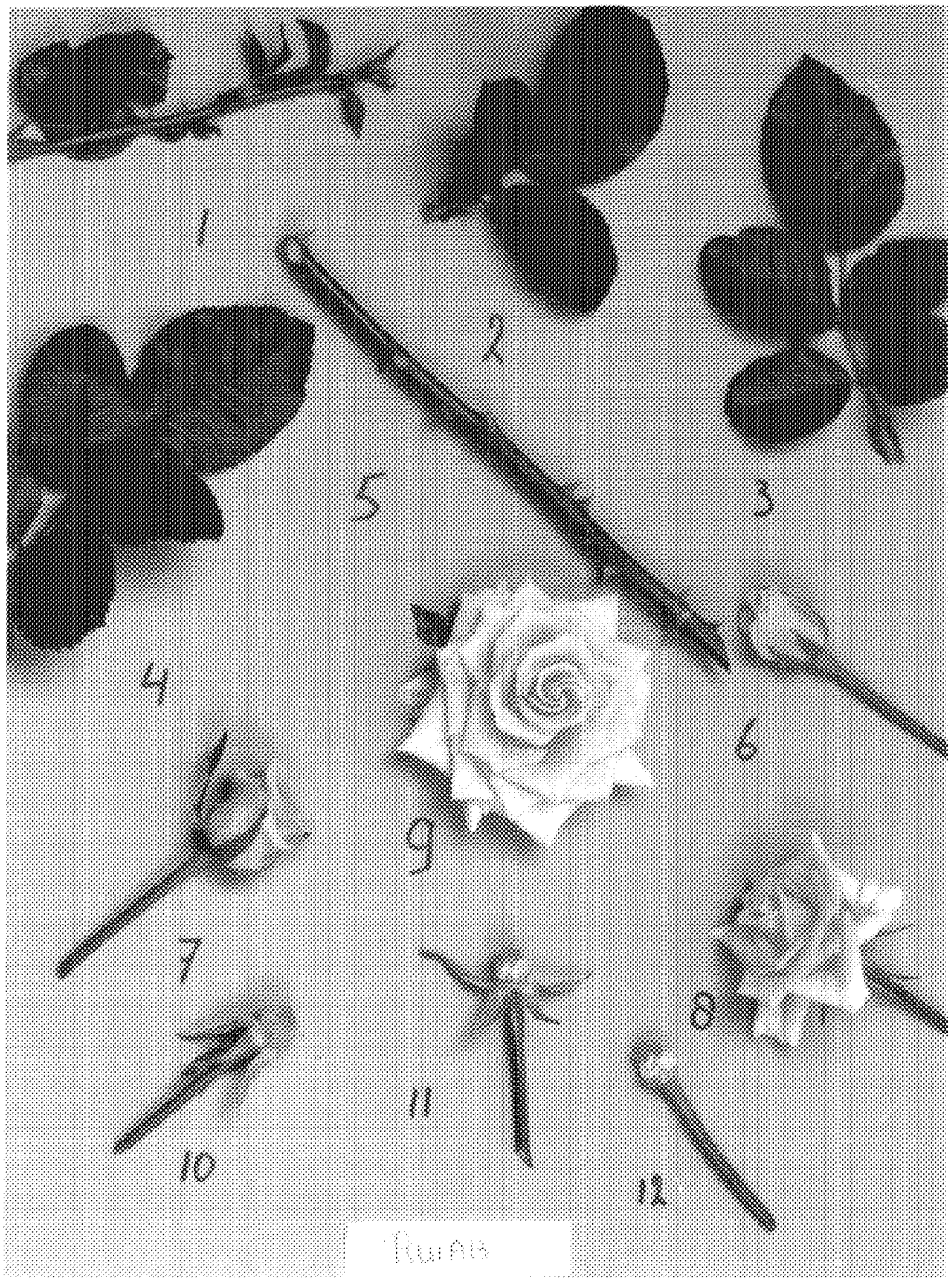
1
2
3
4
5
6
7
8
9
10
11
12
Rune